(12) United States Patent
Hattori et al.

(10) Patent No.: US 8,835,173 B2
(45) Date of Patent: Sep. 16, 2014

(54) SUBSTRATE FOR CELL CULTURE

(75) Inventors: Hideshi Hattori, Shinjuku-ku (JP); Norihiko Okochi, Shinjuku-ku (JP); Masatoshi Kuroda, Shinjuku-ku (JP); Kazunari Ikeda, Shinjuku-ku (JP)

(73) Assignee: Dai Nippon Printing Co., Ltd., Tokyo (JP)

( * ) Notice: Subject to any disclaimer, the term of this patent is extended or adjusted under 35 U.S.C. 154(b) by 1110 days.

(21) Appl. No.: 11/754,568

(22) Filed: May 29, 2007

(65) Prior Publication Data
US 2007/0274968 A1 Nov. 29, 2007

(30) Foreign Application Priority Data
May 29, 2006 (JP) ................................. 2006-148552

(51) Int. Cl.
*C12N 5/00* (2006.01)

(52) U.S. Cl.
CPC .......... *C12N 5/0068* (2013.01); *C12N 2533/30* (2013.01); *C12N 2535/10* (2013.01)
USPC ............................. 435/395; 435/325; 435/404

(58) Field of Classification Search
USPC .......................................... 435/404, 325, 395
See application file for complete search history.

(56) References Cited

U.S. PATENT DOCUMENTS

| 2005/0136536 A1* | 6/2005 | Anderson et al. ............. 435/366 |
| 2005/0208656 A1 | 9/2005 | Miyake et al. |
| 2007/0122901 A1 | 5/2007 | Morita et al. |
| 2007/0233274 A1 | 10/2007 | Miyake |
| 2007/0259328 A1 | 11/2007 | Morita et al. |

FOREIGN PATENT DOCUMENTS

| JP | 2003-009860 A | 1/2003 |
| JP | 2004-321040 A | 11/2004 |
| JP | 2005-052011 A | 3/2005 |
| JP | 2005/160441 A | 6/2005 |
| JP | 2005-342112 A | 12/2005 |
| WO | WO 03/010302 A1 | 2/2003 |
| WO | 2005/038011 A1 | 4/2005 |
| WO | 2005/099784 A1 | 10/2005 |

OTHER PUBLICATIONS

Japanese Office Action issued in corresponding JP Application No. 2006-148552 on Oct. 4, 2011.
Office Action issued in corresponding Japanese Patent Application No. 2012-137683 on Jan. 15, 2013.

* cited by examiner

*Primary Examiner* — Ruth Davis
(74) *Attorney, Agent, or Firm* — Sughrue Mion, PLLC

(57) ABSTRACT

An object of the present invention is to provide a means capable of transferring a cell sheet, a cell pattern or the like to a desired material at a high speed. The present invention provides a substrate for cell culture comprising a base and a cell adhesive region formed on a surface of the base, wherein the cell adhesive region is formed of a film that is rendered cell adhesive by applying an oxidation treatment and/or a decomposition treatment to a cell-adhesion inhibitory hydrophilic film containing an organic compound having a carbon-oxygen bond.

6 Claims, 2 Drawing Sheets

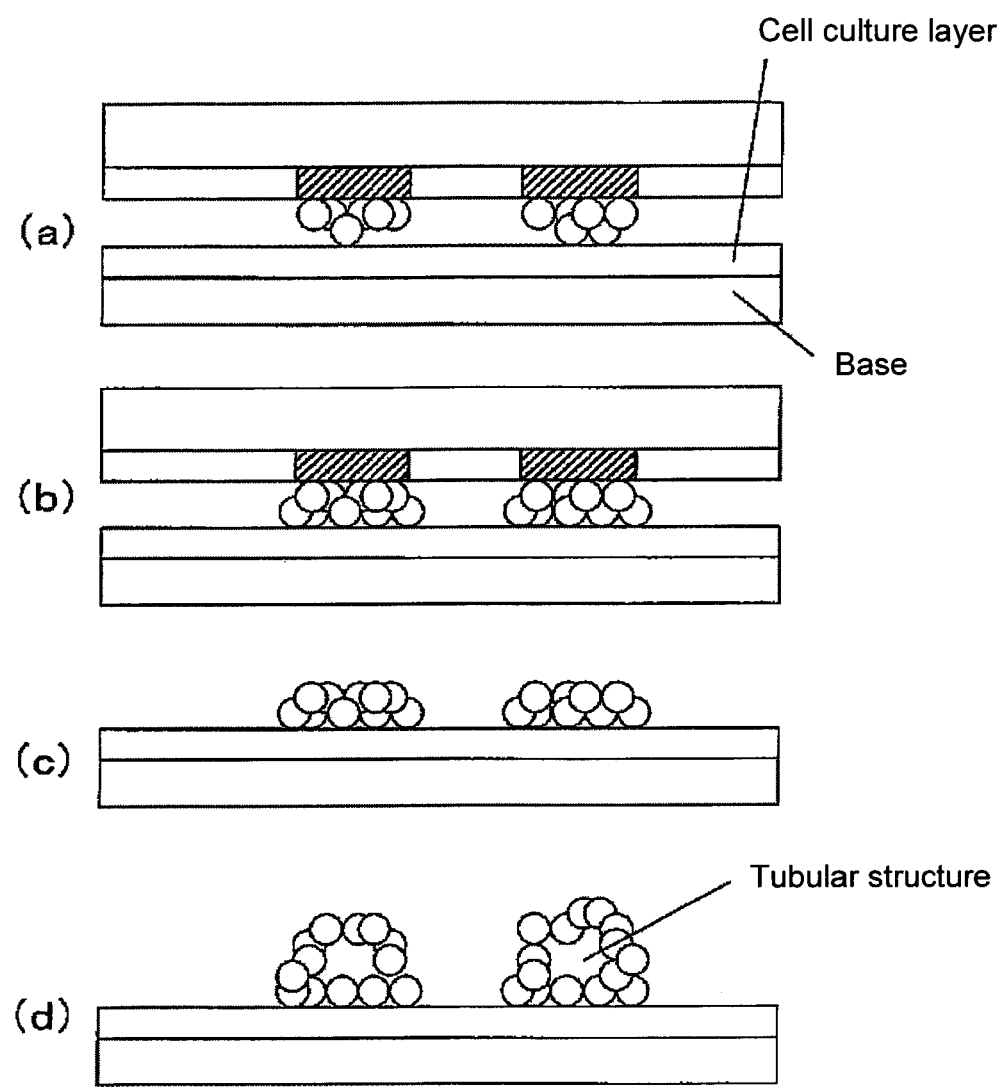

SUBSTRATE FOR CELL CULTURE

BACKGROUND OF THE INVENTION

1. Field of the Invention

The present invention relates to a substrate for cell culture capable of transferring cells grown in adhesion culture to a cell sheet, an organ and a protein sheet, etc., while keeping the cells alive, for use in processing of cells and regenerative medicine.

2. Background Art

At present, various types of animal cells and vegetable cells have been cultured and novel cell-culture methods have been developed. Cell-culture technique has been used to elucidate biochemical phenomena and properties of cells and produce useful substances. Furthermore, to check physiological activities and toxicity of artificially synthesized medicaments, the cultured cells are used. Moreover, recently, researchers have intensively studied on regenerative medicine for transplanting cells or tissue cultured by an in vitro cell-culture step, to a patient.

Some types of cells (in particular, most animal cells) are known to grow while anchoring (adhering) to something. Since they have such adhesion dependency, cells cannot survive for a long time in vitro in a floating state. When the cells having the adhesion dependency are cultured, a carrier must be used for attaching the cells. In general, a plastic culture plate uniformly coated with a cell adhesive protein such as collagen or fibronectin is used. These cell adhesive proteins are known to act on cultured cells to facilitate adhesion of the cells and exert an effect upon morphogenesis of the cells.

On the other hand, there is a report on a technique for adhering cultured cells only to a small limited portion of a substrate to align the cells. This technique makes it possible to apply cultured cells to artificial organs, biosensors and bioreactors, etc. Cultured cells are usually aligned by use of a surface-patterned substrate constituted of regions different in cell adhesiveness. When cells are cultured on the surface-patterned substrate, cells adhere only to an adhesive surface, thereby aligning the cells.

For example, JP Patent Publication (Kokai) No. 02-245181A (1990) discloses that cells are cultured by use of a charge retaining medium having an electrostatic pattern formed thereon for proliferating the nerve cells in a circuit form. JP Patent Publication (Kokai) No. 03-7576A (1991) discloses that photolithographic patterning is applied to a substrate formed of a cell-adhesive or non-adhesive photosensitive hydrophilic polymer and cells are cultured on the patterned surface of the substrate to align the cultured cells.

Furthermore, JP Patent Publication (Kokai) No. 05-176753A (1993) discloses a substrate for cell culture having a pattern formed of a substance such as collagen, which influences a cell-adhesion ratio and morphology of cells, and a method of preparing the substrate by photolithography. When cells are cultured on such a substrate, a larger number of cells adhere onto the surface coated with collagen, etc. In this manner, patterning of cells is performed.

However, depending upon the usage thereof, patterns on a substrate for cell culture must be formed with high accuracy. When patterning is photolithographically performed using a photosensitive material as mentioned above, a highly precise pattern can be obtained; however, in this case, a cell adhesive material must have photosensitivity. Unfortunately, it is often difficult to chemically impart photosensitivity to a biopolymer etc. A cell adhesive material must be selected from an extremely narrow range. In addition, in photolithographic method using a photoresist, a developing solution and the like must be used. These solutions sometimes have adverse effects upon cell culture.

Furthermore, to form a precise pattern of a cell adhesive material, a micro-contact printing method is proposed by George M. Whitesides of Harvard University (e.g., U.S. Pat. Nos. 5,512,131 and 5,900,160 and JP Patent Publication (Kokai) Nos. 9-240125A (1997) and 10-12545A (1998). However, it is difficult to industrially apply this method in manufacturing a cell culture substrate having a patterned cell adhesive material.

Recently, a technique for transferring viable cells cultured in accordance with a pattern to tissues and organs and a tissue formed by the technique have been reported (JP Patent Publication (Kokai) No. 2005-342112A and WO 2005/038011). However, this technique has problems. Since it takes a long time to transfer cells, intricate operations are required for maintaining the activity of the cells.

SUMMARY OF THE INVENTION

An object of the present invention is to provide a means for making it possible to transfer a cell sheet, sporadically attached cells, cell colonies, cell network, patterned cells and so forth to a cell sheet, tissue, organ, protein sheet and so forth, at a high speed.

The present invention encompasses the following inventions.

(1) A substrate for cell culture comprising a base and a cell adhesive region formed on a surface of the base, in which the cell adhesive region is formed of a film that is rendered adhesive by applying an oxidation treatment and/or a decomposition treatment to a cell-adhesion inhibitory hydrophilic film containing an organic compound having a carbon-oxygen bond.

(2) A substrate for cell culture comprising a base and a cell adhesive region and a cell adhesion inhibitory region formed on a surface of the base, in which the cell adhesive region is formed of a film that is rendered adhesive by applying an oxidation treatment and/or a decomposition treatment to a cell-adhesion inhibitory hydrophilic film containing an organic compound having a carbon-oxygen bond, and the cell adhesion inhibitory region is formed of a hydrophilic film containing an organic compound having a carbon-oxygen bond.

(3) The substrate for cell culture according to item (1) or (2), in which the decomposition treatment is performed by oxidation or UV irradiation.

(4) A substrate for cell culture comprising a base and a cell adhesive region formed on a surface of the base, in which the cell adhesive region is formed of a hydrophilic film containing an organic compound having a carbon-oxygen bond, and the density of the organic compound in the cell adhesive region is sufficiently low for cells to adhere.

(5) A substrate for cell culture comprising a base and a cell adhesive region and a cell adhesion inhibitory region formed on a surface of the base, in which the cell adhesive region and the cell adhesion inhibitory region are formed of a hydrophilic film containing an organic compound having a carbon-oxygen bond, and a density of the organic compound in the cell adhesive region is lower than a density of the organic compound in the cell adhesive inhibitory region.

(6) The substrate for cell culture according to any one of items (2) to (5), in which the amount of carbon in the cell adhesive region is 20 to 99% relative to the amount of carbon in the cell adhesion inhibitory region.

(7) The substrate for cell culture according to any one of items (2) to (6), in which the ratio (%) of carbon binding to oxygen relative to carbon in the cell adhesive region is 35 to 99% based on the ratio (%) of carbon binding to oxygen relative to carbon contained in the cell adhesion inhibitory region.

(8) The substrate for cell culture according to any one of items (1) or (7), in which the organic compound having a carbon-oxygen bond is an alkylene glycol based material.

(9) A cell-adhered substrate comprising the substrate for cell culture according to any one of items (1) or (8) and cells that adhere to the cell adhesive region of the substrate for cell culture.

(10) A method of forming a tissue comprising a step of transferring cells present on the cell-adhered substrate according to item (9) to a target material.

(11) The method according to item (10) in which the step is performed in a plurality of times.

(12) A tissue formed by the method according to item (10) or (11).

The present invention makes it possible to transfer a cell sheet sporadically attached cells, cell colonies, cell network, patterned cells and so forth to a cell sheet, tissue, organ, protein sheet and so forth, at a high speed.

BRIEF DESCRIPTION OF THE DRAWINGS

FIG. 2 shows a procedure for transferring cells from the cell-adhered substrate to a target material and how to culture the cells.

DETAILED DESCRIPTION OF THE PREFERRED EMBODIMENTS

Figure 1:
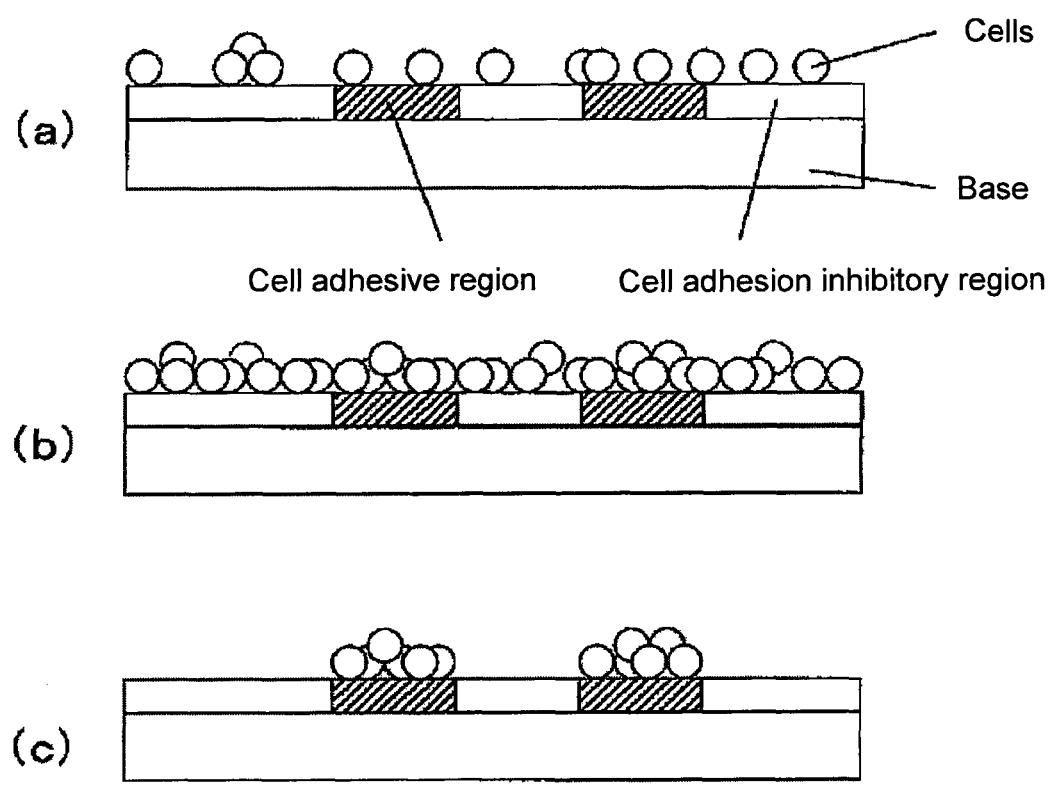
FIG. 1 shows a procedure for forming a cell-adhered substrate.

A substrate for cell culture (hereinafter referred to as "cell-culture substrate") according to the present invention is characterized by comprising a base and a cell adhesive region formed on the surface of the substrate.

On the surface of the base, not only the cell adhesive region but also a cell adhesion inhibitory region is preferably formed. More preferably, the cell adhesive regions and the cell adhesion inhibitory regions are arranged in accordance with a pattern.

The term "cell adhesiveness" used herein means adhesion force, that is, cell-adhesion susceptibility. The "cell adhesive region" refers to a region having good cell adhesiveness, whereas the "cell adhesion inhibitory region" refers to a region having poor cell adhesiveness. When cells are seeded on a substrate having the cell adhesive regions and the cell adhesion inhibitory regions arranged in accordance with a pattern, the cells adhere to the cell adhesive regions but do not adhere to the cell adhesion inhibitory regions. As a result, cells are arranged in accordance with the pattern on the surface of the cell-culture substrate.

The cell adhesiveness varies depending upon the cells that are to adhere. "Good cell adhesiveness" means that the "cell adhesiveness" to a certain type of cells is good. Therefore, when a plurality of cell adhesive regions are present corresponding to a plurality types of cells, respectively, at least two types of cell adhesive regions having different degrees of cell adhesiveness may present.

A cell-culture substrate according to the present invention is characterized by the structure of the cell adhesive region. In the present invention, the structure of the cell adhesive region can be roughly divided into two types of structures.

In a first structure, the cell adhesive region is formed of a film, which is rendered adhesive by applying an oxidation treatment and/or a decomposition treatment to a cell adhesion inhibitory hydrophilic film containing an organic compound having a carbon-oxygen bond. In the first structure, first, the cell adhesion inhibitory hydrophilic film containing an organic compound having a carbon-oxygen bond is formed over the entire surface of a base. Then, an oxidation treatment and/or a decomposition treatment is applied to a region to which cells are desired to adhere. In this manner, cell adhesiveness is imparted to the desired region, which is converted into a cell adhesive region. The region to which no treatment is applied becomes the cell adhesion inhibitory region. If the oxidation treatment and/or decomposition treatment is applied to the entire surface of the cell adhesion inhibitory hydrophilic film, a cell-culture substrate comes to have only the cell adhesive region.

In a second structure, a cell adhesive region is formed of a hydrophilic film, which contains an organic compound having a carbon-oxygen bond in a low density. A hydrophilic film, if it contains an organic compound having a carbon-oxygen bond in a high density, exhibits a cell adhesion inhibitory property. In contrast, a hydrophilic film, if it contains such an organic compound in a low density, exhibits cell adhesiveness. The second structure uses such a property. More specifically, the surface of a base is formed so as to contain a first region to which the organic compound easily adheres and a second region to which the organic compound does not virtually adhere. Then, a film of the organic compound is formed on the surface of the base. As a result, the first region becomes the cell adhesion inhibitory region and the second region becomes the cell adhesive region.

The following explanation will be applied to either one of the two structures mentioned above unless otherwise specified.

<Base>

The base to be employed as the cell-culture substrate of the present invention is not particularly limited. Any base material may be used as long as a film of an organic compound having a carbon-oxygen bond can be formed on the surface thereof. Specific examples of the base material include inorganic materials such as metal, glass, ceramic and silicon, and organic materials such as elastomer and plastic (e.g., polyester resin, polyethylene resin, polypropylene resin, ABS resin, nylon, acrylic resin, fluorine resin, polycarbonate resin, polyurethane resin, methylpentene resin, phenol resin, melamine resin, epoxy resin and vinyl chloride resin). The shape of the base is not particularly limited. Examples of the shape include a planar shape such as a flat plate, flat membrane, film or porous film and a three-dimensional shape such as a cylinder, stamp, multi-well plate or micro channel may be mentioned. When a film is employed, the thickness of the film is not particularly limited; however, the thickness is generally 0.1 to 1000 µm, preferably 1 to 500 µm, and more preferably, 10 to 200 µm.

<Cell Adhesion Inhibitory Region>

The cell adhesion inhibitory region is formed of a hydrophilic film formed of an organic compound having a carbon-oxygen bond. The hydrophilic film is a thin film formed of an organic compound having a carbon-oxygen bond, soluble in water and swollen with water, as a main material. The hydrophilic film is not particularly limited and any hydrophilic film may be used as long as it has a cell adhesion inhibitory property before oxidized and/or decomposed and it acquires cell adhesiveness after it is oxidized and/or decomposed.

In the "carbon-oxygen bond" of the present invention refers to the bond to be formed between carbon and oxygen. The carbon-oxygen bond may not be limited to a single bond and includes a double bond. Examples of the carbon-oxygen bond include a C—O bond, a C(=O)—O bond and a C=O bond.

Examples of the main material include water-soluble polymers, water-soluble oligomers, water-soluble organic compounds, surfactants and amphipathic substances. They are physically or chemically crosslinked with each other and physically or chemically bind to a base to form a hydrophilic thin film.

Specific examples of the water-soluble polymers include polyalkylene glycols and derivatives thereof, polyacrylic acids and derivatives thereof, polymethacrylic acids and derivatives thereof, polyacrylamide and derivatives thereof, polyvinyl alcohols and derivatives thereof, bipolar-ion type polymers and polysaccharides. As a molecular configuration, linear, branched and dendrimer configurations may be mentioned. More specific examples thereof include, but not limited to, polyethylene glycol, a copolymer of polyethylene glycol and polypropylene glycol such as pluronic F108, pluronic F127, poly(N-isopropylacrylamide), poly(N-vinyl-2-pyrrolidone), poly(2-hydroxyethylmethacrylate), poly(methacryloyloxyethylphosphoryl choline), a copolymer of methacryloyloxyethylphosphoryl choline and an acrylic monomer, dextran and heparin.

Specific examples of the water-soluble oligomers and water-soluble low molecular-weight compounds include alkylene glycol oligomers and derivatives thereof, acrylic oligomers and derivatives thereof, methacrylic oligomers and derivatives thereof, acrylamide oligomers and derivatives thereof, saponificated vinyl acetate oligomers and derivatives thereof, oligomers formed of bipolar-ion monomers and derivatives thereof, acrylic acids and derivatives thereof, methacrylic acids and derivatives thereof, acrylamide and derivatives thereof, bipolar ion compounds, water soluble silane coupling agents, and water-soluble thiol compounds. More specific examples thereof include, but not limited to, ethylene glycol oligomer, (N-isopropylacrylamide)oligomer, methacryloyloxyethylphosphoryl choline oligomer, low molecular-weight dextran, low molecular-weight heparin, oligo(ethylene glycol)thiol, ethylene glycol, diethylene glycol, triethylene glycol, tetraethylene glycol, 2-[methoxy(polyethyleneoxy)propyl]trimethoxysilane and triethyleneglycol-terminated thiol.

The hydrophilic film desirably has a high cell adhesion inhibitory property before oxidation and/or decomposition treatment and exhibits weak cell adhesiveness after the oxidation and/or decomposition treatment.

The average thickness of the hydrophilic film is preferably 0.8 nm to 500 μm, more preferably, 0.8 nm to 100 μm, further preferably, 1 nm to 10 μm, and most preferably, 1.5 nm to 1 μm. The average thickness is preferably 0.8 nm or more because a protein is adsorbed and cells adhere without any influence from the region of a base not covered with a hydrophilic thin film. When the average thickness is 500 μm or less, coating can be relatively easily performed.

The hydrophilic film may be formed on the surface of a base by a method of adsorbing a hydrophilic organic compound directly to a base, a method of coating a base directly with a hydrophilic organic compound, a method of coating a base with a hydrophilic organic compound, followed by applying a crosslinking treatment, a method of forming hydrophilic thin films stepwise in order to increase the adhesiveness to a base, a method of forming an underlying layer on a base to improve adhesiveness with the base and then coating the base with a hydrophilic organic compound, or a method of forming a polymerization initiation point on the surface of a base and polymerizing a hydrophilic polymer to form a hydrophilic polymer brush.

Of the film formation methods mentioned above, mention may be particularly preferably made of a method of forming hydrophilic thin films stepwise, and a method of forming an underlying layer on a base to improve adhesiveness with the base and then coating the base with a hydrophilic organic compound. This is because the adhesiveness of a hydrophilic organic compound to a base can be easily improved by these methods. The term "binding layer" is used in the present invention. When thin films of a hydrophilic compound are formed stepwise, the "binding layer" refers to the layers present between the outermost hydrophilic thin film layer and the base. On the other hand, when an underlying layer is formed on the surface of the base and a hydrophilic thin film is formed on the underling layer, the "binder layer" refers to the underlying layer. The binding layer is preferably a layer containing a material formed of a compound having a binding portion (linker). Examples of a combination of the linker and a functional group at an end of the material to be linked to the linker, include a combination of an epoxy group and a hydroxyl group, a combination of phthalic anhydride and a hydroxyl group, a combination of a carboxyl group and N-hydroxysuccinimide, a combination of a carboxyl group and a carbodiimide, and a combination of an amino group and glutaraldehyde. In each of the combinations, either one of the groups may serve as a linker. In these methods, before applying coating with a hydrophilic layer, a binding layer is formed on the base by a material formed of a compound having a linker. The density of the material formed of the binding layer is an important factor defining the binding force. The density can be easily evaluated by using the contact angle of water with the surface of the binding layer as a reference index. For example, in a silane coupling agent (epoxy silane) having an epoxy group at an end, if the contact angle of water with the surface of a substrate to which epoxy silane was added is typically 45° or more, and desirably, 47° or more, a substrate having a sufficient cell adhesion inhibitory property can be formed by adding an ethylene glycol based material etc. in the presence of an acid catalyst.

<Formation of a Cell Adhesive Region by Oxidation Treatment and/or Decomposition Treatment of a Hydrophilic Film>

In the first embodiment of the present invention, the cell adhesive region is formed of a film, which is rendered to be cell adhesive by applying an oxidation treatment and/or a decomposition treatment to a cell adhesion inhibitory hydrophilic film containing an organic compound having a carbon-oxygen bond. The cell adhesive region thus formed is relatively weak in cell adhesiveness. Therefore, cells that adhere onto the region can be transferred to a material having a relatively strong interaction with cells such as a protein sheet, cell sheet, tissue and organ, at a high speed.

In the present invention, the term "oxidation" refers to oxidation of a narrow sense, that is, refers to a reaction for binding an organic compound with oxygen, thereby increasing the oxygen content before the reaction.

In the present invention, the term "decomposition" refers to a change where a single organic compound is changed into at least two organic compounds by cutting a bond of the single organic compound. Examples of the "decomposition treatment" typically include, but not limited to, decomposition with an oxidation treatment and decomposition with UV irradiation. In the decomposition treatment with an oxidation treatment, that is, oxidation decomposition, the "decomposition treatment" may be identical to the "oxidation treatment".

The decomposition with UV irradiation refers to a decomposition where an organic compound is excited by absorbing UV rays and then decomposed. Note that when UV rays are applied to a system in which an organic compound is present together with a molecular species are containing oxygen such as oxygen and water, the organic compound is decomposed by absorbing UV rays. Besides this, the molecular species are activated by UV rays and react with the organic compound. The latter reaction is classified into "oxidation". The decomposition reaction of an organic compound through oxidation by the activated molecular species can be not classified into "decomposition by UV rays" but classified into "decomposition by oxidation".

As described above, the "oxidation treatment" and the "decomposition treatment" are partially overlapped in view of operation and thus cannot be clearly distinguished. For this reason, the present invention employs the term "oxidation treatment and/or decomposition treatment".

Examples of the oxidation treatment and/or decomposition treatment of a hydrophilic film include a treatment with UV rays, a treatment with a photo catalyst and a treatment with an oxidizing agent. More specifically, the entire or part of the surface of the hydrophilic film may be treated with the oxidization treatment and/or decomposition treatment. When the part of the hydrophilic film is treated with the oxidization treatment and/or decomposition treatment, it would be better to use a mask such as a photomask or a stencil mask, or a stamp. Alternatively, the oxidization treatment and/or decomposition treatment may be directly performed by a laser such as UV laser.

When UV rays is applied, it is preferred to employ a light source emitting UV rays having a wavelength from a VUV region to a UV-C region such as a mercury lamp emitting UV rays having a wavelength of 185 nm to 254 nm or an excimer lamp emitting UV rays having a wavelength of 172 nm. When a photo catalyst treatment is performed, a light source emitting UV rays having a wavelength of 365 nm or less is preferable and more preferably a light source emitting UV rays of 254 nm or less. As the photo catalyst, it is preferred to use a titanium oxide photo catalyst, or a titanium oxide photo catalyst activated with a metal ion or a metal colloid. As the oxidizing agent, any organic acid and inorganic acid may be used without particular limitation. However, such an acid is preferably used as a diluted solution of 10% or less because it is difficult to handle an acid of a high concentration. An optimal treatment time period with UV rays, a photo catalyst, or an oxidizing agent can be appropriately set depending upon various conditions such as the UV intensity of the light source to be used, the activity of the photo catalyst, and oxidizing power and concentration of the oxidizing agent.

<Formation of Cell Adhesive Region by Reducing the Density of an Organic Compound Forming of the Hydrophilic Film>

In the second embodiment of the present invention, the cell adhesive region is formed of a hydrophilic film containing an organic compound having a carbon-oxygen bond in a low density. The cell adhesive region thus formed is also relatively weak in cell adhesion performance. Therefore, the cells that adhere onto the cell adhesive region can be transferred to a material having a relatively strong interaction with cells such as a protein sheet, cell sheet, tissue and organ.

In this embodiment of the present invention, both of the cell adhesive region and the cell adhesion inhibitory region are formed of a hydrophilic film containing an organic compound having a carbon-oxygen bond. However, the two regions differ in density of the organic compound mentioned above. The higher the density of the organic compound, the more difficult the cells adhere. In the cell adhesive region, the density of the organic compound is sufficiently low for cells to adhere. On the other hand, in the cell adhesion inhibitory region, the density of the organic compound is too high for cells to adhere.

The density of a hydrophilic organic compound can be controlled by forming a binding layer between the thin film of a hydrophilic organic compound and the surface of a base and controlling the binding force between the binding layer and the hydrophilic organic compound. The "binding layer" used herein is the same as defined above and may be formed of the aforementioned preferable material. The binding force of the binding layer increases as the density of a material formed of a compound having a linker in the binding layer increases, whereas the binding force decreases as the density decreases. The density of the material formed of a compound having a linker in the binding layer can be evaluated by using the contact angle of water with the surface of the binding layer as a reference index, as described above.

In the embodiment of the present invention, the density of a material formed of a compound having a linker of the binding layer in the cell adhesive region is low. The contact angle of water with the surface of the binding layer before the thin film of a hydrophilic organic compound is formed in the cell adhesive region is typically 10° to 43°, desirably 15° to 40°, taking a silane coupling (epoxy silane) agent having an epoxy group at an end as an example of the material formed of a compound having a linker. Such a binding layer may be formed by forming a film (binding layer) of a material formed of a compound having a linker on the surface of a base and applying the oxidation treatment and/or decomposition treatment to the surface of the binding layer. The oxidation treatment and/or decomposition treatment may be performed by irradiating the surface of the binding layer with UV rays, treating the surface of the binding layer with a photocatalyst or an oxidizing agent. The oxidation treatment and/or decomposition treatment may be applied to the whole or part of the surface of the binding layer. The partial treatment may be performed by use of a mask such as a photomask or a stencil mask or a stamp. Also, the oxidation treatment and/or decomposition treatment may be performed by directly applying a laser such as UV laser. The same conditions as used in the case of forming the cell adhesive region by applying the oxidation treatment and/or decomposition treatment to the hydrophilic film may be employed in this case. On the binding layer thus formed, a thin film of a hydrophilic organic compound is formed. In this manner, a cell adhesive region can be formed.

In the embodiment of the present invention, the density of a material formed of a compound having a linker in the binding layer of the cell adhesion inhibitory region is high. The contact angle of water with the surface of the binding layer before a thin film of a hydrophilic organic compound is formed in the cell adhesive inhibitory region is typically 45° or more, and desirably, 47° or more, by taking a silane coupling (epoxy silane) agent having an epoxy group at an end as an example for the material formed of a compound having a linker. Such a binding layer can be obtained by forming a film of a material formed of a compound having a linker, on the surface of a base. When the oxidation treatment and/or decomposition treatment is partially applied to the surface of the binding layer, the remaining portion not treated is the binding layer having the aforementioned contact angle with water. By forming a thin film of a hydrophilic organic compound on the binding layer thus formed, the cell adhesive inhibitory region can be formed.

<Comparison Between the Cell Adhesive Region and the Cell Adhesion Inhibitory Region>

The following explanation will be applied to either one of the two embodiments mentioned above.

The carbon amount of the cell adhesive region (including the binding layer when it is present) is preferably lower than that of the cell adhesion inhibitory region (including the binding layer when it is present). More specifically, the carbon amount of the cell adhesive region is preferably 20 to 99% relative to that of the cell adhesion inhibitory region. It is particularly preferable that the carbon amount falls within the range when the thickness of the hydrophilic film (the total thickness of the hydrophilic film and the binding layer when the binding layer is present) is 10 μm or less. The amount of carbon is expressed by "% by atomic concentration" as defined below.

Furthermore, the ratio of carbon binding to oxygen relative to carbon contained in the cell adhesive region (including the binding layer when it is present) is preferably smaller than that in the cell adhesive inhibitory region (including the binding layer when it is present). More specifically, the ratio (%) of carbon binding to oxygen relative to carbon contained in the cell adhesive region is preferably 35 to 99% relative to that in the cell adhesion inhibitory region. It is particularly preferable that the relation between the two ratios falls within the range when the thickness of the hydrophilic film (the total thickness of the hydrophilic film and the binding layer when the binding layer is present) is 10 μm or less. The ratio of carbon binding to oxygen is expressed by "% by atomic concentration" as defined below.

<Evaluation Method of Hydrophilic Thin Film>

The hydrophilic thin film (including the binding layer when it is present) of the present invention can be evaluated by contact-angle measurement, ellipsometry, atomic force microscopic observation, electron microscopic observation, Auger electron spectroscopy, X-ray photoelectron spectroscopy, and various mass spectroscopies, etc. Of them, the most excellent method is the x-ray photoelectron spectroscopy (XPS/ESCA). The quantitative amount obtained by each of these spectroscopies is a relative value and generally expressed in terms of atomic concentration (%). The X-ray photoelectron spectroscopy of the present invention will be now explained in detail.

<Method for Calculating the Carbon Amount of Hydrophilic Thin Film and Method for Calculating the Ratio of Carbon Binding to Oxygen>

In the present invention, the "carbon amount" of the hydrophilic thin film is defined as the "carbon amount obtained from the analysis value of a C1s peak obtained by means of the X-ray photoelectron spectroscopy". Furthermore, the "ratio of carbon binding to oxygen" of the hydrophilic thin film in the present invention is defined as the "ratio of carbon binding to oxygen obtained from the analysis value of a C1s peak obtained by means of the X-ray photoelectron spectroscopy". Two specific measurement methods thereof will be described below. However, the present invention will not be limited to these measurement methods.

<Measurement Method 1>

X-ray photoelectron spectroscopy: VG_Theta Probe manufactured by Thermo Electron Corporation X-ray source: Monochromic aluminum Kα ray (15 kV–6.67 mA=100W)

Measurement area: 400 μmφ

Positional relationship between a sample and a detector: A lens for taking photoelectrons is set at a position having an angle of 53° with respect to the normal line of the sample Carbon amount: The elements constituting a base and a hydrophilic film are estimated and a photoelectron set to be measured is determined. Based on the total photoelectrons measured, which is regarded as 100%, the concentration of an element derived from each of the photoelectrons is obtained in terms of atomic concentration. The element concentration (% by atomic concentration) of the C1s peak is defined as the carbon amount.

C1s peak fitting method: Peak fitting is performed by use of a C—O bond, C(=O)—O bond, C=O bond, and C—C bond.

Calculation formula for obtaining the ratio of carbon binding to oxygen:

{[the carbon ratio of a C—O bond]+[the carbon ratio of C(=O)—O bond]+[the carbon ratio of C=O bond]}÷{[the carbon ratio of a C—O bond]+[the carbon ratio of a C(=O)—O bond]+[the carbon ratio of C=O bond]+[the carbon ratio of C—C bond]+[(if necessary) the carbon ratio of other bonds]}×100 (%).

Note that, if necessary, other bonds may be added for peak fitting. Based on the data, the concentration of carbon of each bond at a C1s peak is obtained in terms of % by atomic concentration.

<Measurement Method 2>

X-ray photoelectron spectroscopy: ESCA-3400 (Amicus) manufactured by KRATOS analytical X-ray source: Non-monochromic magnesium Kα ray (10 kV-20 mA=200 W)

Measurement area: 6 mmφ

Positional relationship between a sample and a detector: A lens for taking photoelectrons is set on the normal line of the sample Carbon amount: The elements constituting a base and a hydrophilic film are estimated and a photoelectron set to be measured is determined. Based on the total photoelectrons measured, which is regarded as 100%, the concentration of an element derived from each of the photoelectrons is obtained in terms of atomic concentration. The element concentration (% by atomic concentration) of the C1s peak is defined as the carbon amount.

C1s peak fitting method: Peak fitting is performed by use of a C—O bond, C(=O)—O bond, C=O bond, and C—C bond.

Calculation formula for obtaining the ratio of carbon binding to oxygen:

{[the carbon ratio of a C—O bond]+[the carbon ratio of C(=O)—O bond]+[the carbon ratio of C=O bond]}÷{[the carbon ratio of a C—O bond]+[the carbon ratio of a C(=O)—O bond]+[the carbon ratio of C=O bond]+[the carbon ratio of C—C bond]+[(if necessary) the carbon ratio of other bonds]}×100 (%).

Note that if necessary, other bonds may be added for peak fitting. Based on the data, the concentration of carbon of each bond at a C1s peak is obtained in terms of % by atomic concentration.

<Shape of Pattern>

In the cell-culture substrate of the present invention, the cell adhesive regions and the cell adhesion inhibitory regions are preferably arranged in accordance with a pattern. The shape of pattern is not particularly limited as long as it is a two dimensional pattern and can be selected depending upon conditions such as the type of cells and the tissue to be formed.

Examples of the pattern include linear, tree (dendriform), reticular, lattice, circular, and square patterns. A figure such as a circle or a square whose inside opening is entirely occupied by a cell adhesive region or a cell adhesion inhibitory region, may be included as the pattern. When the vascular endothelial cells or nerve cells are cultured to form tissue, it is preferable to align adhesion cells in accordance with a linear, tree (dendriform), reticular, or lattice pattern. The cells aligned in accordance with such a pattern are transferred to a material and cultured. In the vascular endothelial cells aligned in a linear, tree (dendriform), reticular or lattice pattern, tissue formation of cells can be facilitated, that is, vasculogenesis is accelerated. When linear, tree (dendriform), reticular or lattice pattern is formed, the line width of the pattern is generally 20 to 200 µm and preferably 30 to 100 µm. In particular, to form a capillary vessel by aligning vascular endothelial cells linearly and culturing them, the vascular endothelial cells preferably adhere linearly by using a pattern (cell-adhesiveness change pattern) in which linear cell adhesive regions and linear cell adhesion inhibitory regions are alternately arranged. In this case, it is preferred to form a pattern having a line width to which about 1 to 10 cells and preferably 1 to 6 cells sufficiently adhere. More specifically, the line width of the cell adhesive region is generally 20 to 200 µm and preferably 30 to 80 µm. The width of the space between lines, in other words, the width (space) of the cell adhesion inhibitory region, is generally 80 to 1000 µm, and preferably, 100 to 800 µm. By setting the line width within the aforementioned numerical range, vascular endothelial cells can be efficiently developed into tubular tissue. Since vascular endothelial cells can adhere linearly by such a cell-adhesiveness change pattern, when the vascular endothelial cells thus linearly arranged are transferred, they successfully and efficiently develop into tissue to form a capillary vessel. When it is desired to form a cell pattern having a plurality of lines arranged in parallel without intersecting, it is preferable that the space width between cell adhesion lines is set at the aforementioned predetermined value or more. If the space width satisfies the numerical condition, it is possible to prevent pseudopodium from extending from a cell to the space between lines and deforming a line when cells develop into tissue.

<Cells>

As the cells to be seeded onto the cell-culture substrate, floating cells such as hemocytes and lymphocytes and adhesive cells each may be used. However, the present invention may be suitably applied to the adhesive cells. Examples of the adhesive cells include the parenchymal cells of the liver, namely, hepatic cells, Kupffer cells, endothelial cells such as vascular endothelial cells and cornea endothelial cells, fibroblasts, osteoblasts, osteotomy cells, cells originated from the periodontal membrane, epidermic cells such as epidermal keratinocytes, trachea epithelial cells, epithelial cells of digestive organs, uterine cervix epithelial cells, epithelial cells such as corneal epithelial cells, milk glandular cells, pericytes, muscle cells such as smooth muscle cells and cardiac muscle cells, kidney cells, pancreas Langerhans' cells, nerve cells such as peripheral nerve cells and visual nerve cells, chondrocytes, and bone cells. These cells may be either first-generation cells directly taken from tissues or organs or several-generation cells taken from a subculture of them. Furthermore, these cells may be undifferentiated cells such as embryonic stem cells or multipotent stem cells having pluripotency such as mesenchyme system stem cells, unipotent stem cell having unipotency such as vascular endothelial precursor cells, or differentiated cells. In addition, a single type of cells or a mixture of at least two types of cells may be cultured.

<Cell-Adhered Substrate>

The present invention provides a cell-adhered substrate comprising a cell-culture substrate and cells that adhere onto a cell adhesive region of the cell-culture substrate. The cell-adhered substrate may be distributed as a commercially available product.

A method for forming a cell-adhered substrate will be explained with reference to FIG. 1. FIG. 1 shows an example of a method in which the cell-culture substrate having a cell adhesive region and a cell adhesion inhibitory region on the base us employed. This is used just for explanation. A method in which a cell-culture substrate having only a cell adhesive region over the surface on the base is employed is also encompassed in the range of the present invention.

As shown in FIG. 1(a), cells are seeded uniformly over the surface of a cell-culture substrate. The cells are cultured for a predetermined time period as shown in FIG. 1(b). When the substrate is washed to remove extra cells present in the cell adhesion inhibitory region, the cell-adhered substrate having a cell pattern formed of cells that adhere onto the cell adhesive region and vacant spaces (no cells) on the cell adhesion inhibitory region can be obtained, as shown in FIG. 1(c).

A culturing sample containing desired cells is preferably subjected to a pre-treatment such as a dispersion treatment for making a living tissue into pieces and dispersing them in a liquid or a separation treatment for removing contaminants such as cells except for desired cells and cell debris of the living tissue.

In advance to seeding of cells onto the cell-culture substrate, the culturing sample containing desired cells is preferably pre-cultured by any one of culture methods to proliferate the desired cells. As the pre-culture, a general culture method such as monolayer culture, coat-dish culture or culture on gel may be employed. As one of the pre-culture methods for culturing cells while attaching them on the surface of a support, a so-called monolayer culture is already known. To explain this method more specifically, a culture vessel containing a culturing sample and a culture solution is maintained in constant environmental conditions. As a result, predetermined viable cells are only proliferated while adhering onto the surface of the support such as a culture vessel. The apparatus and process conditions to be employed are set in accordance with a general monolayer culture method. As the material for the support surface on which cells adhere and proliferate, a material such as polylysine, polyethylene imine, collagen and gelatin suitable for adhesion and proliferation of cells may be selected. Alternatively, a chemical substance facilitating adhesion and proliferation of cells called a "cell adhesion factor" may be applied onto the surface of the support such as a glass plate, plastic plate, slide glass, cover glass, plastic sheet or plastic film.

After completion of the pre-culture, the culture solution is removed from the culture vessel to eliminate unnecessary components such as massive or fibrous contaminants non-adhesive to the surface of the support from the culture sample. In this manner, only viable cells that adhere to the surface of the support can be collected. When the viable cells that adhere to the surface of the support are recovered by an EDTA-trypsin treatment.

The cells pre-cultured as mentioned above are seeded on a cell-culture substrate placed in a culture solution as shown in FIG. 1(a). The method and amount of seeding cells are not particularly limited. For example, the method described in "tissue culture method (1999)", p 266-270 (edited by the Japanese Tissue Culture Association and published by Asakura Publishing Co. Ltd.). It is preferred to seed cells in a sufficient amount (not necessary to proliferate any more) on a cell-culture substrate such that they can mutually adhere to form a monolayer. Generally, cells are preferably seeded such that a culture solution contains $10^4$ to $10^6$ cells/ml, and that cells are contained $10^4$ to $10^6$ cells/substrate (cm$^2$). This is because when the cells are coagulated, development of cells into tissue is inhibited, and the function of cells decreases even if they are transferred to a target material and cultured. More specifically, cells are seeded in a ratio of about $2 \times 10^5$ cells per 400 mm$^2$.

It is preferable to allow cells to adhere to the cell adhesive region by culturing a cell-culture substrate having cells seeded thereon in a culture solution. A culture solution is not particularly limited and any culture solution may be used as long as it is a cell culture medium generally used in the art. For example, a basal medium as described in "tissue culture method" the third edition, p 581 (edited by the Japanese Tissue Culture Association and published by Asakura Publishing Co. Ltd.) such as MEM medium, BME medium, DME medium, α MEM medium, IMDM medium, ES medium, DM-160 medium, Fisher medium, F12 medium, WE medium and RPMI1640 medium may be used in accordance with the type of cells to be used. Furthermore, the basal medium may be supplemented with serum (such as fetal bovine serum), various growth factors, antibiotics, and amino acids. Moreover, a commercially available serum-free medium such as Gibco serum-free medium (manufactured by Invitrogen) may be used. In consideration of clinical application of the cellular tissue finally obtained, a culture medium free from components of an animal origin is preferably used.

As shown in FIG. 1(b), a step of culturing cells is performed in order to allow the cells to adhere onto the cell adhesive region of the cell-culture substrate. The culture time varies depending upon the presence or absence of manipulation of cells during a culture process. The culture time is generally 6 to 96 hours and preferably 12 to 72 hours. If cells are cultured in an appropriate period of time, when washed, cells can be removed from the cell adhesion inhibitory region of the cell-culture substrate, whereas remain on the cell adhesive region thereof by an appropriate adhesion force. Therefore, the remaining cells can be easily transferred to a target material.

The culture temperature is generally 37° C. It is preferable to culture cells in a cell culture apparatus under an atmosphere containing about 5% $CO_2$. After completion of culture, a cell-culture substrate is washed to remove cells that do not adhere on the substrate. In this manner, a cell-adhered substrate according to the present invention having cells that adhere onto the cell adhesive region can be formed.

<Application of Cell-Adhered Substrate>

How to transfer the cells to a target material and how to culture the cells after transfer by use of on the cell-adhered substrate obtained in accordance with the procedure mentioned above will be explained. FIG. 2 shows the case in which vascular endothelial cells are transferred to a target material having a cell culture layer provided on the surface of a base, as an example. However, the present invention is not limited to this.

As is shown in FIG. 2(a), a cell-adhered substrate, which is a cell-culture substrate having cells that adhere onto the cell adhesive region thereof, is brought into contact with the cell culture layer of a target material. Then, as shown in FIG. 2(b), the cells are cultured to allow the cells to adhere onto the cell culture layer of the target material. Since the adhesion force of the cells onto the cell adhesive region is lower than that of the cell culture layer, the cells are transferred to the target material by removing the cell-culture substrate from the target material, as shown in FIG. 2(c). When the cells thus transferred are further cultured, the cells become functional. In this case, when the cells are vascular endothelial cells, a tubular structure can be regenerated, as shown in FIG. 2(d).

The target material to which cells are to be transferred is not particularly limited. Any material may be used as long as it can adhere cells and the cells can cultured on it. However, a material having an adhesive surface to which cells can adhere more strongly than the cell adhesive region of the cell-culture substrate is preferred. To explain more specifically, to stably develop cells into tissue, a target material desirably has a soft surface and an appropriate cell adhesion force (adhesion force may not be too strong) as is described in the following reference (Mechanochemical switching between growth and differentiation during fibroblast growth factor-stimulated angiogenesis in vitro: Role of extracellular matrix. Donald E. Ingber et al. J. of cell biol. (1989) p. 317). Particularly preferably, a cell sheet, tissue, organ, protein sheet, biological gel, and protein coat can be used as target materials, as is specifically described below.

Examples of a preferable target material that may be used include a collagen sheet, fibrin sheet, elastin sheet and amnion sheet. When the cell culture layer (described later) is provided on a base, a material of the base is not particularly limited. Any material may be used as long as it cannot inhibit culture of cells performed on the cell culture layer. Examples of the material that may be used include glass, polystyrene, polyethylene terephthalate, polycarbonate, polyimide, polylactic acid, polyglycolic acid, poly(lactic acid-glycolic acid) copolymer, polycaprolactone and poly(glycerol-sebacate). Also, materials exemplified as materials for the base of a cell-culture substrate can be used.

The cell culture layer may contain a chemical substance and cell adhesion factor that suitably facilitate adhesion and proliferation of cells on the surface. Examples of these substances include extracellular substances such as various types of collagen substances, fibronectin, laminin, vitronectin, cadherin, gelatin, peptide and integrin. These may be used singly or in a mixture of two or more types. Because of strong cell-adhesiveness, various types of collagen substances are preferably used. Of the various type of collagen substances, type I collagen and type IV collagen are particularly preferably used. Alternatively, the cell culture layer may be formed of an extracellular substance produced by culturing extracellular-substance producing cells such as osteoblasts.

The shape of the target material is not particularly limited. Any target material may be used as long as it has a surface to which cells can be transferred. For example, a culture plate such as Petri dish or a multi-dish may be used. Furthermore, a culture plate formed of glass or plastic as mentioned above may be used.

The transfer of cells from the cell-adhered substrate to a target material can be performed by bringing the cell adhesion surface of the cell-adhered substrate into contact with the surface of the target material, for example, the cell culture layer. When cells are cultured while the cell-adhered substrate and the target material are in contact with each other in this manner, the cells are successfully transferred. Culturing conditions may be appropriately selected depending upon the substrate and cells to be employed; however, cells are generally cultured in conditions: a $CO_2$ concentration of 5%, 37° C., for 15 minutes to 96 hours, preferably 30 minutes to 36 hours.

Thereafter, cells are cultured in a culture solution. Cells may be cultured while the cell-adhered substrate and the target material are in contact with each other. Alternatively, after the cell-adhered substrate is removed, cells may be cultured on the target material. Preferably, after cells are cultured for a predetermined period of time while the cell-adhered substrate and the target material are in contact with each other, the cell-adhered substrate is removed and then cells are further cultured. Culture conditions are not particularly limited and can be selected depending upon the type of cells to be cultured. As a culture solution, any one of the culture solutions as mentioned above may be used.

In the cell-adhered substrate of the present invention, cells adhering in accordance with a pattern can be easily transferred to the target material while maintaining the pattern of cells. After the cells are transferred, the cell-adhered substrate is washed and used again as a cell-adhered substrate for seeding cells. A cell pattern can be formed again and transferred for culturing. Therefore, cell pattern can be inexpensively and efficiently formed. Since it is not necessary to form a specific pattern on the target material, any material may be used as the target material as long as it is generally used in culturing. Therefore, a target material can be chosen from a wide variety of materials. In addition, cells are not influenced by a harmful substance contained in a developing solution.

A biological material may be included in the target material. The biological material refers to a material derived from a living body such as tissues and organs. Specific examples thereof include organs such as lung, heart, liver, kidney, brain, stomach, the small intestine and large intestine, and tissues such as bone, cartilage, skin, muscle, eyeball, tongue and peritoneum. Furthermore, cell masses such as a cell sheet and spheroid can be also used as the target material. Examples of the cells forming a cell mass include cells producing an extracellular substance such as interstitial cells, epithelial cells and parenchyma cells. Specific examples of the cells that may be preferably used include osteoblasts, fibroblasts, hepatic parenchymal cells and feeder cells.

When the cells on the cell-culture substrate are directly transferred to such a biological substance, cells can be directly cultured on tissue and an organ in accordance with a pattern. Examples of a combination of a biological material to which cells are to be transferred and cells to be transferred to the biological material for culturing include a combination of the liver and vascular endothelial cells, a combination of the dermis and vascular endothelial cells, a combination of the osteoblast layer and vascular endothelial cells, a combination of the fibroblast layer and hepatic parenchymal cells, a combination of endothelial cell layer and hepatic parenchymal cells, and a combination of a feeder cell layer and corneal epithelial cells.

In such an embodiment, since cells can be directly transferred to a biological material such as an organ and cultured, it is not necessary to recover cells by removing them from a cell culturing carrier with enzymatic treatment. Therefore, damage of cells can be prevented.

In organ transplantation, a capillary vessel is formed on the surface of the transplanted organ. It is known that transplantation can be more efficiently performed after a capillary vessel is formed on the surface of the organ to be transplanted. However, in a conventional method in which a capillary vessel is formed and attached on the surface of the organ to be transplanted before transplantation, it takes much time to form the capillary vessel. As a result, high-speed transplantation of the organ cannot be performed. In addition, when the capillary vessel previously formed on a culture substrate is removed from the substrate and transferred to the surface of an organ, tissue may be damaged. In the method of the present invention, after cells arranged in accordance with a pattern on the cell-adhered substrate are transferred on the surface of an organ, the organ is transplanted before a capillary vessel is completely formed. Therefore, transplantation can be performed at a high speed. Since vascular endothelial cells arranged linearly or reticularly and transferred onto the surface of an organ can easily develop into tissue, in vivo capillary vasculogenesis can be facilitated. Furthermore, in the present invention, since a treatment for removing cells from the cell-culture substrate is not required when the cells are transferred, a problem such as tissue damage does not occur. Moreover, in the present invention, since transfer of cells can be performed at a high speed, tissue or organ is less affected.

When the transferred cells are cultured, a cell stimulation factor may be added as needed. The cell stimulation factor is effective in enhancing the activity of the cells and expression of inherent function of cells to promote the formation of tissue. As a cell stimulation factor, any substance may be used as long as it has an activity of facilitating tissue formation of cells. Examples of such a substance include a vascular endothelial cell growth factor (VEGF), fibroblast growth factor (FGF), nerve growth factor (NGF), epithelial cell growth factor (EGF) and insulin-like growth factor (IGF).

When a step of transferring cells on the cell-adhered substrate to a target material is performed a plurality of times, a multi-layered tissue can be formed.

The present invention is also directed to a tissue formed by a method including a step of transferring cells on the cell-adhered substrate to a target material. When a transfer step is performed a plurality of times, the obtained tissue has a multiple layered structure. When a target material is a living tissue or organ, the tissue formed on the living tissue or organ is encompassed in the scope of the present invention.

The present invention is also directed to a method including permitting cells derived from a subject to adhere onto a cell-culture substrate of the present invention in accordance with a pattern, transferring the patterned cells to the surface of living tissue of the subject, such as an organ, skin or bone, and proliferating the cells, thereby regenerating the tissue of the subject. The subject is not particularly limited. For example, a mammal, and preferably, a human, may be mentioned. For example, when the dermis fibroblast cells or epithelial cells are directly transferred to a damaged portion of the skin of a living body of a subject and proliferated, a skin tissue can be regenerated in the subject. Furthermore, when vascular endothelial cells are transferred in accordance with a pattern to a damaged skin portion of a subject, and proliferated to form a capillary vessel, regeneration of the skin can be facilitated. Moreover, when nerve cells are arranged in accordance with a pattern and cultured, a nerve cell circuit and a nerve cell computer can be formed.

EXAMPLES

Example 1

<Preparation of Cell-Culture Substrate>
<First-Step Reaction>

First, 39.0 g of toluene and 13.5 g of epoxy silane TSL8350 (manufactured by GE Toshiba Silicones Co., Ltd.) were mixed. While the mixture solution was stirred, a catalyst amount of triethylamine was added. The mixture was further stirred at room temperature for several minutes. A UV washed glass substrate of 10 cm square was soaked in the epoxy silane solution prepared above and allowed to stand still at room temperature for 12 hours. Thereafter, the glass substrate having the underlying layer formed thereon washed with ethanol, followed with water and dried. The average contact angle of water with the surface of the substrate after the film formation was 50.2°.
<Second Step Reaction>

While 50 g of tetraethylene glycol was stirred, a catalyst amount of concentrated sulfuric acid was slowly added. The mixture was further stirred at room temperature for several minutes. The epoxylated substrate prepared above was soaked in the tetraethylene glycol solution prepared above. The reaction was performed at 80° C. for 20 minutes. After completion of the reaction, the substrate washed well with water and then dried. In this manner, a glass substrate having a hydrophilic thin film formed thereon was successfully formed.
<Oxidation Treatment>

A quartz plate coated with a titanium oxide-base photo catalyst was prepared. The luminous intensity of a light exposure apparatus was measured at a wavelength of 350 nm and used as a reference for setting light exposure time. The luminous intensity was 20 mW/cm$^2$. The glass substrate having a hydrophilic thin film formed thereon and the quartz plate coated with the photo catalyst were arranged such that the hydrophilic thin film faced the photo catalyst layer and then placed in the light exposure apparatus such that the rear surface of the quartz plate was irradiated with light. Oxidation treatment was performed by applying light for 25 seconds. Thereafter, the glass substrate was cut into pieces of 24 mm×15 mm so as to easily handle it in a culture process.
<Surface Analysis>

Using VG_Thera Probe manufactured by Thermo Electron Corporation, the carbon amount of the hydrophilic thin film was measured before and after the oxidation treatment. The carbon amount of the hydrophilic thin film was obtained by performing C is peak fitting with carbon of a C—C bond carbon, C—O bond carbon, C(=O)—O bond and C=O bond. The carbon amount of the hydrophilic thin film after oxidation treatment was 92.2% relative to that before the oxidation treatment. The ratio of carbon binding to oxygen in the hydrophilic thin film before the oxidation treatment was 60.8% and that after the oxidation treatment was 59.2%.
<Cell Culture>

The cut pieces of the substrate prepared above were sterilized with high-pressure vapor in an autoclave. The substrate pieces were arranged in a culture vessel and 2.6×10$^5$ of bovine vascular endothelial cells (bECs) were seeded per substrate piece. The substrate pieces were cultured in MEM medium containing 5% serum in an incubator of 5% $CO_2$ concentration at 37° C. for 46 hours. When observed by a phase-contrast microscope, bECs adhered confluently to the substrate pieces.
<Transfer of Cells>

The culture vessel was placed on ice and 200 µl of a growth factor reduced Matrigel (manufactured by Becton Dickinson) was added in the culture vessel and spread by a cell scraper cooled to 4° C. until to the same size as that of the cell-adhered substrate. Thereafter, the culture vessel was allowed to stand still at room temperature for about 5 minutes to gelate Matrigel. On the gelated Matrigel, the cell-adhered substrate was gently placed such that the cell adhesion surface faced Matrigel. The bECs were allowed to be in contact with Matrigel for several minutes. Thereafter, MEM medium containing 0.3% serum was added to the culture vessel, which was then placed in an incubator of a 5% $CO_2$ concentration at 37° C. Two hours later, the cell-culture substrate alone was easily and successfully removed. When observed by a phase-contrast microscope, it was confirmed that that almost 100% of bECs were transferred to Matrigel.

Comparative Example 1

<Preparation of Cell-Culture Substrate>

The UV washed glass substrate used in Example 1 was cut into pieces of 24 mm×15 mm.
<Cell Culture>

The cut pieces of the substrate prepared above were sterilized with high-pressure vapor in an autoclave. The substrate pieces were arranged in a culture vessel and cultured for 46 hours in the same conditions as in Example 1. When observed by a phase-contrast microscope, bECs confluently adhered to the substrate pieces.
<Transfer of Cells>

The bECs were allowed to be in contact with Matrigel for several minutes in the same manner as in Example 1. Subsequently, MEM medium containing 0.3% serum was added to the culture vessel, which was then kept in an incubator of a 5% $CO_2$ concentration at 37° C. Two hours later, when the cell-culture substrate was removed, bECs were not transferred. Another bEC sample was cultured for a further 2.5 hours. After bECs were cultured for 4.5 hours in total, the cell-culture substrate was removed. As a result, a cell transfer ratio was 20%.
<Surface Analysis>

Using VG_Thera Probe manufactured by Thermo Electron Corporation, the carbon amount of the UV washed glass substrate sterilized with high pressure vapor was measured. A C1s peak was fitted with carbon of a C—C bond carbon, C—O bond carbon, C(=O)—O bond and C=O bond. The ratio of carbon binding to oxygen was 32.0%.

Example 2

<Preparation of Cell-Culture Substrate>
<First-Step Reaction>

First, 19.5 g of toluene and 6.8 g of epoxy silane TSL8350 (manufactured by GE Toshiba Silicones Co., Ltd.) were mixed. While the mixture was stirred, a catalyst amount of triethylamine was added. The reaction was further stirred at room temperature for several minutes. A UV washed glass substrate of 10 cm square was soaked in the epoxy silane solution prepared above and allowed to stand still at room temperature for 14 hours. Subsequently, the epoxylated glass substrate washed with ethanol followed by water and dried. An average contact angle of water with the surface of the substrate after the film formation was 51.4°.
<Second Step Reaction>

While 25 g of tetraethylene glycol (TEG) was stirred, a catalyst amount of concentrated sulfuric acid was slowly added. The mixture was further stirred for several minutes. The epoxylated substrate prepared above was soaked in TEG. The reaction was performed at 80° C. for 15 minutes. After completion of the reaction, the substrate washed well with water and then dried. In this manner, a glass substrate having a hydrophilic thin film formed thereon was successfully formed.
<Oxidation Treatment>

A photomask coated entirely with a titanium oxide-base photo catalyst was prepared. The photomask had a size of 5 inches. In the photomask, a line pattern having opening portions of 60 µm width were formed at intervals (pitches) of 300 µm and linear opening portions of 60 µm width arranged at intervals of 2.5 cm were formed so as to cross in perpendicular to the line pattern. In addition, an opening portion of about 1.5 cm width was formed in the periphery of the photomask. The luminous intensity of a light exposure apparatus was previously measured at a wavelength of 350 nm and used as a reference for setting light exposure time. The luminous intensity was 20 mW/cm². The glass substrate having a hydrophilic thin film formed thereon and the photomask coated with an photo catalyst were arranged such that the hydrophilic thin film faced the photo catalyst layer of the photomask and placed in the light exposure apparatus such that the rear surface of the photomask was irradiated with light. Oxidation treatment was performed by applying light for 75 seconds. Thereafter, the glass substrate was cut into pieces of 24 mm×15 mm so as to easily handle it in a culture process.

<Surface Analysis>

Using VG_Thera Probe manufactured by Thermo Electron Corporation, the carbon amounts of the glass substrate base, the hydrophilic thin film before the oxidation treatment, and a region of the hydrophilic thin film after the oxidation treatment, which region corresponded to the opening portion of about 1.5 cm width in the peripheral portion of the photomask, were measured. A C1s peak was fitted with C—C bond carbon, C—O bond carbon, C(=O)—O bond and C=O bond. The carbon amount of the oxidized region of the hydrophilic thin film was 89.9% relative to that of the unoxidized region of the hydrophilic thin film. The ratio of carbon binding to oxygen in the unoxidized region of the hydrophilic thin film was 71.9%, and that of the oxidized region of the hydrophilic thin film was 47.6%. Note that a glass plate used as a substrate was measured, the ratio of carbon binding to oxygen was 30.2%.

<Cell Culture>

The cut pieces of the substrate prepared above were sterilized with high-pressure vapor in an autoclave. The substrate pieces were arranged in a culture vessel and 1.5×10⁵ of human umbilical vein endothelial cells (HUVEC) manufactured by Kurabo Industries Ltd. were seeded per substrate piece. A low-serum medium for proliferating normal human vascular endothelial cells, HuMedia-EG2 (manufactured by Kurabo Industries Ltd.) was added to a final cell concentration of $1.2 \times 10^5$ cells/ml. The cells were cultured in an incubator of a 5% $CO_2$ concentration at 37° C. for 46 hours. When observed by a phase-contrast microscope, HUVECs confluently adhered only to the oxidized portion.

<Transfer of Cells>

The culture vessel was placed on ice and 200 µl of a growth factor reduced Matrigel (manufactured by Becton Dickinson) was added in the culture vessel and spread by a cell scraper cooled to 4° C. until to the same size as that of the cell-adhered substrate. Thereafter, the culture vessel was allowed to stand still at room temperature for about 5 minutes to gelate Matrigel. On the gelated Matrigel, the cell-adhered substrate was gently placed such that the cell adhesion surface faced Matrigel. The cell pattern was allowed to be in contact with Matrigel for several minutes. Thereafter, HuMedia-EG2 was added to the culture vessel, which was then placed in an incubator of a 5% $CO_2$ concentration at 37° C. Thirty minutes later, when observed by a phase-contrast microscope, it was confirmed that a tubular configuration of HUVECs was formed. The cell-culture substrate alone was easily and successfully removed. HUVECs were almost completely (100%) transferred to Matrigel. When observed by a phase contrast microscope, it was confirmed that the tubular configuration was not substantially disturbed.

Example 3

<Preparation of Cell-Culture Substrate>
<First-Step Reaction>

First, 39.0 g of toluene and 13.5 g of epoxy silane TSL8350 (manufactured by GE Toshiba Silicones Co., Ltd.) were mixed. While the mixture was stirred, 450 µl of triethylamine was added. After the mixture was stirred as it was at room temperature for several minutes, the total amount of the mixture was transferred to a glass plate. Into this, a UV washed glass substrate of 10 cm square was soaked and allowed to stand still at room temperature for 16 hours. Thereafter, the glass substrate washed with ethanol and water and dried with nitrogen blow. In this manner, a thin film containing an epoxy group was formed on the surface of the glass substrate. An average contact angle of water with the substrate surface after the film formation was 48.9°.

<Second Step Reaction>

While 50 g of TEG was stirred, 250 µl of concentrated sulfuric acid was added dropwise. After the mixture was further stirred for several minutes, the total amount of the mixture was transferred to a glass plate. Into this, the aforementioned substrate was soaked and the reaction was performed at 80° C. for 15 minutes. After completion of the reaction, the substrate washed well with water and then dried with nitrogen blow. In this manner, a hydrophilic thin film was uniformly formed on the glass surface of the substrate.

<Oxidation Treatment>

A photomask coated with a photo catalyst as used in Example 2 was used herein. The photo catalyst layer of the photomask was brought into contact with the hydrophilic thin film on the surface of the substrate and placed in the light exposure apparatus such that the rear surface of the photomask was irradiated with light. Light was applied by a mercury lamp having a luminous intensity of 20 mW/cm² at a wavelength of 350 nm, for 50 seconds to oxidatively decompose a part of the hydrophilic thin film of the substrate surface. The substrate was cut into pieces of 24 mm×15 mm and used as cell-culture substrates.

<Surface Analysis>

Using ESCA-3400 (Amicus) manufactured by KRATOS Analytical, element analysis was performed with respect to an oxidized region and an unoxidized region by photo catalyst lithography. The carbon amount of the oxidized region of the hydrophilic thin film was 63.8% relative to that of the unoxidized region thereof. The ratio of carbon binding to oxygen in the unoxidized region of the hydrophilic thin film was 71.9%, and that of the oxidized region thereof was 62.6%.

<Cell Culture>

The substrates were sterilized in an autoclave and arranged in a culture vessel, to which MEM medium containing 5% bovine serum was added in an appropriate amount. Then, 2.0×10⁵ bovine vascular endothelial cells (bECs) were seeded per substrate and cultured in an incubator (37° C., 5% $CO_2$) for 40 hours. When observed by a phase-contrast microscope, bECs adhered only to a region of relatively low carbon concentration to form a cell pattern.

<Transfer of Cells>

First, 200 µl of a growth factor reduced Matrigel (manufactured by Becton Dickinson) cooled on ice was spread over the culture vessel and allowed to stand still at room temperature for about one minute. Thereafter, the aforementioned substrate was gently placed on Matrigel such that the cell adhesion surface thereof faced down. The substrate was maintained for about 5 minutes in this state to completely gelate Matrigel. Thereafter, MEM medium was added to soak the substrate. The culture vessel was transferred to an incubator (37° C., 5% $CO_2$ concentration) to culture the bECs sandwiched between the substrate and Matrigel. Two hours later, bECs were observed by a phase-contrast microscope. As a result, the width of the cell pattern decreased by about several tens %. At this time, when the substrate was removed, all bECs were already transferred to the gel. The culture vessel was returned to the incubator and cultured for one hour. A tubular structure was formed of bECs in the gel.

Example 4

<Preparation of Cell-Culture Substrate>
<First-Step Reaction>

First, 39.0 g of toluene, 0.48 g of epoxy silane TSL8350 (manufactured by GE Toshiba Silicones Co., Ltd.) and 0.97 g of triethylamine were mixed. The mixture was stirred at room temperature for 10 minutes. To the silane solution, a UV washed glass plate of 10 cm square was soaked such that the washed surface faced up. After the glass plate was allowed to stand still at room temperature for 16 hours, the substrate washed with ethanol and water and dried with nitrogen blow. In this manner, a thin film containing an epoxy group was formed on the surface of the glass substrate. An average contact angle of water with the substrate surface after the film formation was 47.2°.

<Oxidation Treatment>

A photomask coated with a photo catalyst as used in Example 2 was used herein. The photo catalyst layer of the photomask was brought into contact with the organic thin film formed on the surface of the substrate and placed in the light exposure apparatus such that the rear surface of the photomask was irradiated with light. Light was applied by a mercury lamp having a luminous intensity of 20 mW/cm at a wavelength of 350 nm, for 25 seconds to oxidatively decompose a part of the organic thin film of the substrate surface. An average contact angle of water with the surface of the substrate in the region corresponding to the 1.5 cm-width opening portion in the periphery of the mask after the oxidation treatment was 39.7°

<Second Step Reaction>

While 50 g of tetraethylene glycol (TEG) was stirred, 25 µl of concentrated sulfuric acid was added dropwise. After the mixture was stirred as it was for several minutes, the total amount of the mixture was transferred to a glass plate. Into this, the substrate was soaked and the reaction was performed at 80° C. for 15 minutes. After completion of the reaction, the substrate washed well with water and then dried with nitrogen blow. In this manner, a hydrophilic thin film formed of two types of regions mutually different in carbon concentration was formed on the glass substrate surface. The glass substrate was cut into pieces of 25 mm×15 mm, which were used as cell-culture substrates.

<Surface Analysis>

Using ESCA-3400 (Amicus) manufactured by KRATOS Analytical, element analysis was performed with respect to the hydrophilic thin film formed on an oxidized region and that formed on an unoxidized region. The carbon amount of the hydrophilic thin film formed on the oxidized region, that is, in the region containing a hydrophilic material in a low density, was 91.2% relative to that formed on the unoxidized region, that is, in the region containing a hydrophilic material in a high density. The ratio of carbon binding to oxygen in the unoxidized region of the hydrophilic thin film, that is, in the region containing a hydrophilic material in a high density, was 75.1%, and that of the oxidized region, that is, in the region containing a hydrophilic material in a low density, was 70.1%.

<Cell Culture>

The substrates were sterilized in an autoclave and arranged in a culture vessel, to which MEM medium containing 5% bovine serum was added in an appropriate amount. Then, $2.0 \times 10^5$ bovine vascular endothelial cells (bECs) were seeded per substrate and cultured in an incubator (37° C., 5% $CO_2$) for 40 hours. When observed by a phase-contrast microscope, bECs adhered only to a region of a relatively low carbon concentration to form a cell pattern.

<Transfer of Cells>

First, 200 µl of a growth factor reduced Matrigel (manufactured by Becton Dickinson) cooled on ice was spread over the culture vessel and allowed to stand still at room temperature for about one minute. Thereafter, the substrate was gently placed on Matrigel such that the cell adhesion surface thereof faced down. The substrate was maintained for about 5 minutes in this state to completely gelate Matrigel. Thereafter, MEM medium was added to soak the substrate. The culture vessel was transferred to an incubator (37° C., 5% $CO_2$ concentration) to culture the bECs sandwiched between the substrate and Matrigel. One hour later, the bECs were observed by a phase-contrast microscope. As a result, the width of the cell pattern decreased by about several tens %. At this time, when the substrate was removed, all bECs were already transferred to the gel. The culture vessel was returned to the incubator and cultured for one hour. A tubular structure was formed of bECs in the gel.

Example 5

<Preparation of Cell-Culture Substrate>
<First-Step Reaction>

First, 39.0 g of toluene, 0.48 g of epoxy silane TSL8350 (manufactured by GE Toshiba Silicones Co., Ltd.) and 0.97 g of triethylamine were mixed. The mixture was stirred at room temperature for 10 minutes. To the silane solution, a UV washed glass plate of 10 cm square was soaked such that the washed surface faced up. After the glass plate was allowed to stand still at room temperature for 16 hours, the glass plate washed with ethanol and water and dried with nitrogen blow. In this manner, a thin film containing an epoxy group was formed on the surface of the glass substrate surface. The average contact angle of water with the surface of the substrate after the film formation was 49.8°.

<Second Step Reaction>

While 50 g of polyethylene glycol (PEG 400) having an average molecular weight of 400 was stirred, 25 µl of concentrated sulfuric acid was added dropwise. After the mixture was stirred as it was for several minutes, the total amount of the mixture was transferred to a glass plate. Into this, the substrate was soaked and the reaction was performed at 80° C. for 20 minutes. After completion of the reaction, the substrate washed well with water and then dried with nitrogen blow. In this manner, a hydrophilic thin film was uniformly formed on the glass surface of the substrate.

<Oxidation Treatment>

A photomask coated with a photo catalyst as used in Example 2 was used herein. The photo catalyst layer of the photomask was brought into contact with the hydrophilic thin film on the surface of the substrate and placed in the light exposure apparatus such that the rear surface of the photomask was irradiated with light. Light was applied by a mercury lamp having a luminous intensity of 20 mW/cm² at a wavelength of 350 nm, for 50 seconds to oxidatively decompose a part of the hydrophilic thin film of the substrate surface. The substrate was cut into pieces of 25 mm×15 mm and used as cell-culture substrates.

<Surface Analysis>

Using VG_Thera Probe manufactured by Thermo Electron Corporation, element analysis was performed with respect to an oxidized region and an unoxidized region by photo catalyst lithography. The carbon amount of the oxidized region of the hydrophilic thin film was 84.8% relative to that of the unoxidized region of the hydrophilic thin film. The ratio of carbon binding to oxygen in the unoxidized region of the hydrophilic thin film was 72.5%, and that of the oxidized region was 77.1%.
<Cell Culture>
A substrate sterilized in an autoclave was arranged in a culture vessel, to which MEM medium containing 5% bovine serum was added in an appropriate amount. Then, $2.0×10^5$ of bovine vascular endothelial cells (bECs) were seeded per substrate and cultured in an incubator (37° C., 5% $CO_2$) for 24 hours. When observed by a phase-contrast microscope, bECs adhered only to a region of a relatively low carbon concentration to form a cell pattern.

Example 6

<Preparation of Cell-Culture Substrate>
<First-Step Reaction>
First, 39.0 g of toluene and 13.5 g of epoxy silane TSL8350 (manufactured by GE Toshiba Silicones Co., Ltd.) were mixed. While the mixture was stirred, 450 µl of triethylamine was added. After the mixture was stirred at it was at room temperature for several minutes, the total amount of the mixture was transferred to a glass plate. Into this, a UV washed glass substrate of 10 cm square was soaked and allowed to stand still at room temperature for 16 hours. Thereafter, the glass substrate washed with ethanol and water and dried with nitrogen blow. In this manner, a thin film containing an epoxy group was formed on the surface of the glass substrate. An average contact angle of water with the surface of the substrate after the film formation was 52.0°.
<Second Step Reaction>
While 50 g of TEG was stirred, 250 µl of concentrated sulfuric acid was added dropwise. After the mixture was continuously stirred as it was for several minutes, the total amount of the mixture was transferred to a glass plate. Into this, the substrate treated with silane was soaked and the reaction was performed at 80° C. for 15 minutes. After completion of the reaction, the substrate washed well with water and then dried. In this manner, a hydrophilic thin film was uniformly formed on the glass surface of the substrate.
<Oxidation Treatment>
A photomask coated with a photo catalyst as used in Example 2 was used herein. The photo catalyst layer of the photomask was brought into contact with the hydrophilic thin film on the surface of the substrate and placed in the light exposure apparatus such that the rear surface of the photomask was irradiated with light. Light was applied by a mercury lamp having a luminous intensity of 20 $mW/cm^2$ at a wavelength of 350 nm, for 100 seconds to oxidatively decompose a part of the hydrophilic thin film of the substrate surface. The substrate was cut into pieces of 24 mm×15 mm.
<Surface Analysis>
Using VG_Thera Probe manufactured by Thermo Electron Corporation, element analysis was performed with respect to an oxidized region and an unoxidized region by photo catalyst lithography. The carbon amount of the oxidized region of the hydrophilic thin film was 61.8% relative to that of the unoxidized region of the hydrophilic thin film. The ratio of carbon binding to oxygen in the unoxidized region of the hydrophilic thin film was 71.9%, and that of the oxidized region was 44.5%.
(Pattern Adsorption of BSA-FITC)
2 ml of 20 µg/ml BSA-FITC (bovine serum albumin labeled with fluorescein isothiocyanate) was prepared using PBS buffer and transferred to a 35 mm dish. To the BSA-FITC, the aforementioned substrate was soaked such that a hydrophilic thin film of the substrate faced up and allowed to stand still at an incubator (37° C., 5% $CO_2$) overnight. After the substrate washed twice with PBS and the surface of the substrate was observed by a fluorescent microscope. As a result, a clear fluorescent pattern was observed. This is because BSA-FITC was adsorbed only to the oxidized region.

Example 7

<Preparation of Cell-Culture Substrate>
<First-Step Reaction>
First, 39.0 g of toluene and 13.5 g of methacryloyl silane TSL8370 (manufactured by GE Toshiba Silicones Co., Ltd.) were mixed. While the mixture was stirred, 450 µl of triethylamine was added. The mixture was stirred as it was at room temperature for several minutes and the total amount of the mixture was transferred to a glass plate. Into this, a UV washed glass substrate of 5 cm square was soaked and allowed to stand still at room temperature for 16 hours. Thereafter, the glass substrate washed with ethanol and water and dried with nitrogen blow. In this manner, a thin film containing a methacryloyl group was formed on the surface of the glass substrate.
<Second Step Reaction>
To 10 g of polyethylene glycol diacrylate (PEGdA, manufactured by Aldrich), 0.1 g of a polymerizing initiator, 2,2'-dimethoxy-2-phenyl-acetophenone (DMPA, manufactured by Aldrich) was added and dissolved at room temperature. This mixture was applied to the aforementioned methacryloylation substrate by spin coating at 1500 rpm for 5 seconds. Thereafter the entire surface of the substrate was irradiated with UV rays for 3 seconds under a nitrogen atmosphere and post-baked at 160° C. for 10 minutes. The substrate coated with PEGdA was soaked in water overnight and washed with water and then dried. An average dry-film thickness was 0.33 µm.
<Oxidation Treatment>
A general photomask not coated with a photo catalyst and having the same pattern as used in Example 2 was used herein. The mask was gently placed on the PEGdA surface of the substrate coated with PEGdA. The rear surface of the mask was irradiated with UV rays used as a light source, a xenon excimer lamp (172 nm, 10 $mW/cm^2$) under vacuum for one minute. In this manner, the region corresponding to the opening portion of the photomask formed on the surface of the PEGdA film was oxidized. The substrate was cut into pieces of 2.5 cm square, which were used in cell culture.
<Cell Culture>
The substrates were sterilized with 70% ethanol and arranged in a culture vessel, to MEM medium containing 5% bovine serum was added in an appropriate amount. Then $8.3×10^4$ $cells/cm^2$ bovine vascular endothelial cells (bECs) were seeded and cultured in an incubator (37° C., 5% $CO_2$) for 43 hours. When observed by a phase-contrast microscope, bECs adhered only to an oxidized region of the PEGdA film to form a cell pattern.
<Transfer of Cells>
First, 400 µl of a growth factor reduced Matrigel (manufactured by Becton Dickinson) cooled on ice was spread over the culture vessel by use of a cell scraper and allowed to stand still at room temperature for about three minutes. Thereafter, the substrate was gently placed on Matrigel such that the cell adhesion surface thereof faced down. The substrate was maintained for about 5 minutes in this state and MEM medium was added to soak the substrate. The culture vessel was transferred to an incubator (37° C., 5% $CO_2$ concentration) and the bECs sandwiched between the substrate and Matrigel was cultured. Five hours later, bECs were observed by a phase-contrast microscope. As a result, a tubular configuration was formed of cells arranged in a pattern. At this time, when the substrate was removed, bECs were all transferred to the gel.

Example 8

<Preparation of Cell-Culture Substrate>
<First-Step Reaction>

First, 39.0 g of toluene and 0.96 g of methacryloyl silane TSL8370 (manufactured by GE Toshiba Silicones Co., Ltd.) were mixed. While the mixture was stirred, 450 µl of triethylamine was added. The mixture was stirred as it was at room temperature for several minutes, and the total amount of the mixture was transferred to a glass plate. Into this, a UV washed glass substrate of 5 cm square was soaked and allowed to stand still at room temperature for 16 hours. Thereafter, the glass substrate washed with ethanol and water and dried with nitrogen blow. In this manner, a thin film containing a methacryloyl group was formed on the surface of the glass substrate.

<Second Step Reaction>

To a mixture of 8 g of PEGdA (manufactured by Aldrich) and 2 g of 1-vinyl-2-pyrrolidone (VP, manufactured by Tokyo Chemical Industry Co., Ltd), 0.1 g of a polymerizing initiator DMPA (manufactured by Aldrich) was dissolved at room temperature. This mixture was applied to the aforementioned methacrylation substrate by spin coating at 1500 rpm for 5 seconds. Immediately after that, the entire surface of the substrate was irradiated with UV rays for 3 seconds under a nitrogen atmosphere, and then, post-baked at 160° C. for 10 minutes. The substrate coated with PEGdA-VP was soaked in water overnight and washed with water and then dried. An average dry-film thickness was 0.28 µm.

<Oxidation Treatment>

A general photomask not coated with a photo catalyst and having the same pattern as used in Example 2 was used herein. The mask was gently placed on the PEGdA-VP surface of the PEGdA-VP substrate. The rear surface of the mask was irradiated with UV rays used as a light source, a xenon excimer lamp (172 nm, 10 mW/cm$^2$) under vacuum for one minute. In this manner, the region corresponding to the opening portion of the photomask formed on the PEGdA-VP film surface was oxidized. The substrate was cut into pieces of 2.5 cm square, which were used in cell culture.

<Cell Culture>

The substrates were sterilized with 70% ethanol and arranged in a culture vessel, to which MEM medium containing 5% bovine serum was added in an appropriate amount. Then, 8.3×10$^4$ cells/cm$^2$ bovine vascular endothelial cells (bECs) were seeded and cultured in an incubator (37° C., 5% CO$_2$) for 43 hours. When observed by a phase-contrast microscope, bECs adhered only to an oxidized region of PEGdA-VP film to form a cell pattern.

<Transfer of Cells>

First, 400 µl of a growth factor reduced Matrigel (manufactured by Becton Dickinson) cooled on ice was spread over the culture vessel by a cell scraper and allowed to stand still at room temperature for about three minutes. Thereafter, the substrate was gently placed on Matrigel such that the cell adhesion surface thereof faced down. The substrate was maintained in this state for about 5 minutes and MEM medium was added to soak the substrate. The culture vessel was transferred to an incubator (37° C., 5% CO$_2$ concentration) and the bECs sandwiched between the substrate and Matrigel were cultured. Five hours later, bECs were observed by a phase-contrast microscope. As a result, a tubular configuration was formed of cells arranged in a pattern. At this time, when the substrate was removed, bECs were all transferred to the gel.

Example 9

<Preparation of Cell Culture Dish>
<First-Step Reaction>

First, 39.0 g of toluene and 0.48 g of epoxy silane TSL8350 (manufactured by GE Toshiba Silicones Co., Ltd.) were mixed. While the mixture was stirred, 225 µl of triethylamine was added. The mixture was stirred as it was at room temperature for several minutes and the total amount of the mixture was transferred to a glass plate. Into this, a UV washed glass substrate of 10 cm square having a thickness of 0.1 mm was soaked and allowed to stand still at room temperature for 16 hours. Thereafter, the glass substrate washed with ethanol and water and dried with nitrogen blow. In this manner, a thin film containing an epoxy group was formed on the surface of the glass substrate. An average contact angle of water with the substrate surface after the film formation was 49.8°.

<Second Step Reaction>

While 25 g of tetraethylene glycol was stirred, a catalyst amount of concentrated sulfuric acid was slowly added and the mixture was further stirred at room temperature for several minutes. The epoxylated substrate was soaked in the tetraethylene glycol prepared above and the reaction was performed at 80° C. for 60 minutes. After completion of the reaction, the substrate washed well with water and then dried. In this manner, a glass substrate having a hydrophilic thin film formed thereon was formed.

<Oxidation Treatment>

A photomask coated with a photo catalyst used in Example 2 was used herein. The photo catalyst layer of the photomask was brought into contact with the hydrophilic thin film on the surface of the substrate and placed in the light exposure apparatus such that the photomask was irradiated with light. Light was applied by a mercury lamp having a luminous intensity of 18.6 mW/cm$^2$ at a wavelength of 350 nm, for 188 seconds to oxidatively decompose a part of the hydrophilic thin film of the substrate surface. The substrate was cut into pieces of 21 mm×21 mm.

(Dish for Pattern Culture)

A plastic dish (manufacturing by Corning) of 35 mm in diameter having a hole of 14 mm in diameter at the bottom center was used. The aforementioned cell-culture substrate having a thickness of 0.1 mm was allowed to adhere with an adhesive agent KE45T (manufactured by Shin-Etsu Silicones) to the dish so as to cover the bottom hole of the dish. The resultant product was dried at 35° C. for 4 hours, further dried at room temperature for 2 days, sterilized with 70% ethanol, and washed with a phosphate buffer.

<Cell Culture>

In 2.5 ml of MEM medium containing 5% bovine serum, 2×10$^5$ bECs were suspended and seeded on the dish for pattern culture prepared above. This was cultured in an incubator (37° C., 5% CO$_2$) for 68 hours. When observed by a phase contrast microscope, bECs adhered only to the portion of the substrate oxidized.

<Transfer of Cells>

A growth factor reduced Matrigel (200 µl, manufactured by Becton Dickinson) cooled on ice was spread over to about 15 mm in diameter on a tissue-culture plastic sheet (manufactured by Wako Pure Chemical Industries) of 23 mm diameter and allowed to stand still at room temperature for about 10 minutes. The medium in the dish was removed by aspiration. The plastic sheet having Matrigel placed thereon was gently placed such that Matrigel face the pattern-cultured cells on the bottom surface of the dish. The dish was covered by a lid and allowed to stand still at room temperature for about 5 minutes. To this, 2.5 ml of MEM medium containing 0.3% bovine serum was added and the dish was cultured in an incubator (37° C., 5% $CO_2$ concentration) for 3 hours. When observed by a phase-contrast microscope, a tubular configuration was formed of the patterned cells. At this time, when the plastic sheet was removed, all bECs were already transferred to Matrigel on the plastic sheet.

Example 10

<Culture of Fibroblast Cell>
Using a 6-cm dish, murine embryonic fibroblast cells BALB/3T3 clone A31 were cultured in DMEM medium containing a 10% bovine fetus serum. After reached 100% confluent, the cells were further cultured for 24 hours.
<Fluorescent Staining of Bovine Vascular Endothelial Cells>
Bovine vascular endothelial cells (bECs) were stained with fluorescent dye PKH 26 (manufactured by Aldrich) in accordance with manufacturer's protocol.
<Pattern Culture of bECs Stained with Fluorescence>
Using a cell-culture substrate having a thickness of 0.1 mm manufactured in Example 9, bECs stained with a fluorescence dye were cultured in MEM medium containing a 5% bovine fetus serum in an incubator (37° C., 5% $CO_2$ concentration) for 48 hours. Phase-contrast microscopic observation demonstrated that cell pattern was good. Fluorescent microscopic observation demonstrated that bECs were stained well.
<Transfer of Cells>
The medium was removed by aspiration from the dish having fibroblast cells cultured therein. The substrate having bECs stained with a fluorescent dye and pattern-cultured and a fibroblast cell sheet were arranged such that the fibroblast cell sheet faced the pattern-cultured bECs. The dish was covered with a lid and allowed to stand still in an incubator for 10 minutes. Thereafter, to the dish, MEM medium containing 0.3% bovine serum was gently added with care not to move the substrate. The dish was further cultured in an incubator for 6 hours. When observed by a fluorescent microscope, the width of the bEC pattern decreased by about 50%. At this time, the cell-culture substrate was removed with care, and subjected to microscopic observation. As a result, it was found that no bECs were left on the cell-culture substrate, and that the bEC pattern was transferred onto the fibroblast cell sheet.

Example 11

<Substrate Having a Hydrophilic Thin Film Formed Thereon>
A substrate as prepared in Example 2 was used herein.
<Oxidation Treatment>
A photomask was prepared by applying titanium oxide-base photo catalyst to the entire surface. On the photomask (5 inches in size), a pattern was formed having linear opening portions of 60 μm width arranged at intervals of 140 μm and an opening portion of about 1.5 cm width in the peripheral portion thereof. The luminous intensity of a light exposure apparatus was previously measured at a wavelength of 350 nm and used as a reference for setting light exposure time. The luminous intensity was 20 mW/cm². The glass substrate having a hydrophilic thin film formed thereon and the photomask coated with the photo catalyst were arranged such that the hydrophilic thin film faced the catalyst layer of the photomask and placed in the light exposure apparatus such that the rear surface of the photomask was irradiated with light. Oxidation treatment was performed by applying light for 75 seconds. Thereafter, the substrate was cut into pieces of 24 mm×15 mm so as to easily handle it in a culture process.
<Cell Culture and Cell Transfer>
An experiment was performed using HUVECs in the same manner as in Example 2. Even if a density of cell pattern was high, it was confirmed that HUVECs were transferred to Matrigel for 30 minutes in the same manner as in Example 2.

Example 12

<Substrate Having a Hydrophilic Thin Film>
A substrate as prepared in Example 1 was used herein.
<Oxidation Treatment>
A photomask was prepared by applying titanium oxide-base photo catalyst to the entire surface. On the photomask (5 inches in size), a pattern was formed having opening portions of 100 μm square arranged at intervals of 100 μm and an opening portion of about 1.5 cm width in the peripheral portion thereof. The luminous intensity of a light exposure apparatus was previously measured at a wavelength of 350 nm and used as a reference for setting light exposure time. The luminous intensity was 20 mW/cm². The glass substrate having a hydrophilic thin film formed thereon and the photomask coated with the photo catalyst were arranged such that the hydrophilic thin film faced the catalyst layer of the photomask and placed in the light exposure apparatus such that the rear surface of the photomask was irradiated with light. Oxidation treatment was performed by applying light for 25 seconds. Thereafter, the substrate was cut into pieces of 24 mm×15 mm so as to easily handle it in a culture process.
<Cell Culture and Cell Transfer>
An experiment was performed using bECs in the same manner as in Example 1. It was confirmed that even if a square cell pattern of 100 μm square was used, bECs were transferred to Matrigel for 2 hours in the same manner as in Example 1.

What is claimed is:

1. A substrate for cell culture comprising a base and a cell adhesive region formed on a surface of the base and a cell adhesion inhibitory region on the surface of the base, wherein the cell adhesive region is formed of a film that is rendered cell adhesive by applying an oxidation treatment and/or a decomposition treatment to a cell-adhesion inhibitory hydrophilic film containing an organic compound having a carbon-oxygen bond, and wherein the cell adhesion inhibitory region is formed of the hydrophilic film containing an organic compound having a carbon-oxygen bond.

2. The substrate for cell culture according to claim 1, wherein the decomposition treatment is performed by oxidation or UV irradiation.

3. The substrate for cell culture according to claim 1, wherein the amount of carbon in the cell adhesive region is 20 to 99% relative to the amount of carbon in the cell adhesion inhibitory region.

4. The substrate for cell culture according to claim 1, wherein the ratio (%) of carbon binding to oxygen relative to carbon in the cell adhesive region is 35 to 99% based on the ratio (%) of carbon binding to oxygen relative to carbon contained in the cell adhesion inhibitory region.

5. The substrate for cell culture according to claim 1, wherein the organic compound having a carbon-oxygen bond is an alkylene glycol material.

6. A cell-adhered substrate comprising the substrate for cell culture according to claim 1 and cells that adhere to the cell adhesive region of the substrate for cell culture.

\* \* \* \* \*